United States Patent [19]
Yarnitzky

[11] Patent Number: 4,500,411
[45] Date of Patent: Feb. 19, 1985

[54] AUTOMATICALLY OPERATED POLAROGRAPHIC ANALYZER

[75] Inventor: Chaim N. Yarnitzky, Haifa, Israel

[73] Assignee: Technion Research & Development Foundation Ltd., Haifa, Israel; a part interest

[21] Appl. No.: 500,098

[22] Filed: Jun. 1, 1983

[30] Foreign Application Priority Data

Aug. 1, 1982 [IL] Israel ............................. 66438

[51] Int. Cl.³ ............................................. G01N 27/34
[52] U.S. Cl. ..................................... 204/413; 324/440
[58] Field of Search ................. 204/400, 413, 1 T; 239/338; 324/440

[56] References Cited

U.S. PATENT DOCUMENTS

| | | | |
|---|---|---|---|
| 3,210,261 | 10/1965 | Tyler ................................... | 204/413 |
| 3,644,824 | 2/1972 | Barker et al. .................... | 204/413 X |
| 4,007,238 | 2/1977 | Glenn ............................... | 239/338 X |
| 4,125,225 | 11/1978 | Venghiattis ...................... | 239/338 |
| 4,138,322 | 2/1979 | Barnes et al. ..................... | 204/413 |

OTHER PUBLICATIONS

Yarnitzky et al., "Nebulizer for Eliminating Oxygen from Polarographic Flow Cells", Anal. Chem., vol. 48, 1976, pp. 20, 24.

Myers et al., "Determination of Arsenic (III) at the Part-per-Billion Level by D.P.P.", Analytical Chem., vol. 45, No. 2, 2/73, pp. 267-271.

Kennel et al., "A Dual Working Electrode Coulometric Flow-Cell", Journal of Electro. Chem. and Int. Electrochem., vol. 54, No. 1, Jul. 1974, pp. 47-54.

Christie et al., "Constant Potential Pulse Polarography", Analytical Chem., vol. 48, No. 3, Mar. 1976, pp. 561-564.

*Primary Examiner*—G. L. Kaplan
*Assistant Examiner*—Nam X. Nguyen
*Attorney, Agent, or Firm*—Browdy and Neimark

[57] ABSTRACT

The present invention relates to an automatic cell for polarographic analysis. According to the invention said cell comprises a vessel (14) containing a nebulizer (3) for deaerating the sample to be analyzed, the deaerated sample being accumulated into a collector (16) and conveyed to a polarographic cell (15) provided with means for the removal of the sample after its analysis. The automatic polarographic analyzer is characterized by the very short time required for its analysis.

10 Claims, 3 Drawing Figures

AUTOMATICALLY OPERATED POLAROGRAPHIC ANALYZER

BACKGROUND OF THE INVENTION

The present invention relates to a novel cell for polarographic analysis. More particularly, the present invention relates to an automatic cell for polarographic analysis characterized by the very short time required for the analysis in question.

Polarographic analysis was invented about sixty years ago and is defined as a method of analyzing solutions of reducible or oxidizable substances. Today, many chemical elements can be determined by polarographic analysis. The method is also applicable to the analysis of alloys and to many inorganic compounds. It can, in addition, be utilized for the identifications of many organic compounds and for the study of chemical equilibria and rates of reactions in solutions.

The principle of polarography is very simple: The solution to be analyzed is placed in a glass cell containing two electrodes. One electrode consists of a glass capillary tube from which mercury drops slowly (the so-called dropping mercury electrode), the other electrode (the reference electrode) is a pool of mercury or made of some other non-polarizable material.

In recent years, it has become customary to add a third electrode (the counter-electrode) in order to prevent any current flow through the reference electrode.

The cell is connected in series with a galvanometer, which measures the flow of current in an electrical circuit that contains a battery or other source of direct current and a device by means of which the voltage applied to the electrodes can be varied from zero to a few volts. The dropping mercury electrode is usually connected to the negative side of polarizing voltage, and as the voltage is increased by small increments the resulting current is observed on the galvanometer. The current remains very small until the applied voltage reaches a value large enough to cause the substance being determined to be reduced at the dropping mercury electrode. The current then increases rapidly, but it gradually attains a limiting value which remains constant although the voltage is increased further. In qualitative analysis, the voltage required to cause the onset of the rapid increase in current is characteristic of the substance being reduced and serves to identify it. Under appropriate conditions, the final constant limiting current is determined by the rate of diffusion of the reducible substance from the bulk solution to the surface of the mercury drops, and its magnitude is a measure of the concentration of the reducible substance. This renders polarographic analysis quantitative.

About fifty years ago an instrument called polarograph was invented, in which an increasing voltage is applied to the dropping electrode and a curve of current versus voltage (called a polarogram) is recorded.

It is known that electro-analytical methods in general, and sophisticated polarographic methods in particular, such as, e.g. differential pulse polarography, offer several unique advantages over other techniques. They exhibit high sensitivity and high accuracy at moderate to low maintenance costs.

Most instruments utilize the common polarographic cell, which suffers, however from the disadvantage that, prior to the determination, a time-consuming step, the so-called deaeration, is required. This is due to the well known fact that the oxygen dissolved in the solutions to be analyzed interferes with the current measurement. Adequate deaeration—the prior removal of oxygen—usually takes about ten minutes. In a prior communication (Ch. Yarnitzky et al. Anal. Chem. 48 2024, 1976) a description of the operation of a deaeraion device was presented.

Up to now, none of the existing polarographic analyses can be automatically operated, but each sample nevertheless requires much manual handlings as well as deaeration for a relatively long time in the course of its analysis.

SUMMARY AND OBJECTS OF THE INVENTION

It is an object of the present invention, to provide a new type of cell for polarographic analysis which operates fully automatically. It is another object of the present invention to provide an automatic polarographic analyzer which is characterized by the very short time required for its analyses. Thus the invention consists in an automatically operated polarographic analyzer which comprises a vessel containing a nebulizer for deaerating the sample to be analyzed the deaerated sample being accumulated into a collector and conveyed to a polarographic cell provided with means for the removal of the sample after its analysis. Especially suitable for the automatic polarographic analyzer according to the present invention, is a novel mercury valve which enables the analyzed sample to be removed. Also, a mercury valve has a much longer service life than a conventional valve. In addition, other valves do not completely remove the analyzed sample, remnants of which impair the accuracy of subsequent determinations. The automated polarographic cell according to the present invention thus possesses two main advantages:

(1) It eliminates any manual handling steps such as: Introduction of the sample into the polarographic cell proper, deaeration, and removal of the sample after the analysis.

(2) It requires only a very short time for analysis, of the order of about 1 minute, compared with 5 to as much as 15 minutes with the aid of a conventional polarographic cell, provided that one of the known fast-scan polarographic techniques is adopted.

The deaeration of the sample is a very critical and time-consuming step. In principle, it is conceivable to introduce chemical reagents (e.g. sodium sulfite), for the continuous removal of the oxygen with a view to proceeding with the analysis automatically. However, the introduction of a foreign substance could interfere with the polarographic analysis itself, so that deaeration by gaseous nitrogen is the method most commonly used for this purpose. The provision of a nebulizer is accordingly an important feature of the present invention, since on it depends the effectiveness of the deaeration step. The nebulizer is a device based on the venturi pumping effect caused by a stream of nitrogen gas flowing through a short pipe having a constricted inner surface. To the best of our knowledge, up to the present invention no automatic cell for polarographic analysis has been proposed. A few years ago, a multi-cell polarographic analyzer was disclosed, which needed less manual handling then the conventional model; but the time required for the effective removal of oxygen was, in practice, reduced to about 4 to 8 minutes only. Polarographic analyzers of this kind available on the market, were known as Model 374, manufactured by Princeton Applied Research (Princeton, N.J., U.S.A.).

BRIEF DESCRIPTION OF THE DRAWINGS

"The objects and advantages of this invention will be better understood from the following description taken in conjunction with the appended drawings in which.

DETAILED DESCRIPTION ON THE INVENTION

Figure 1:
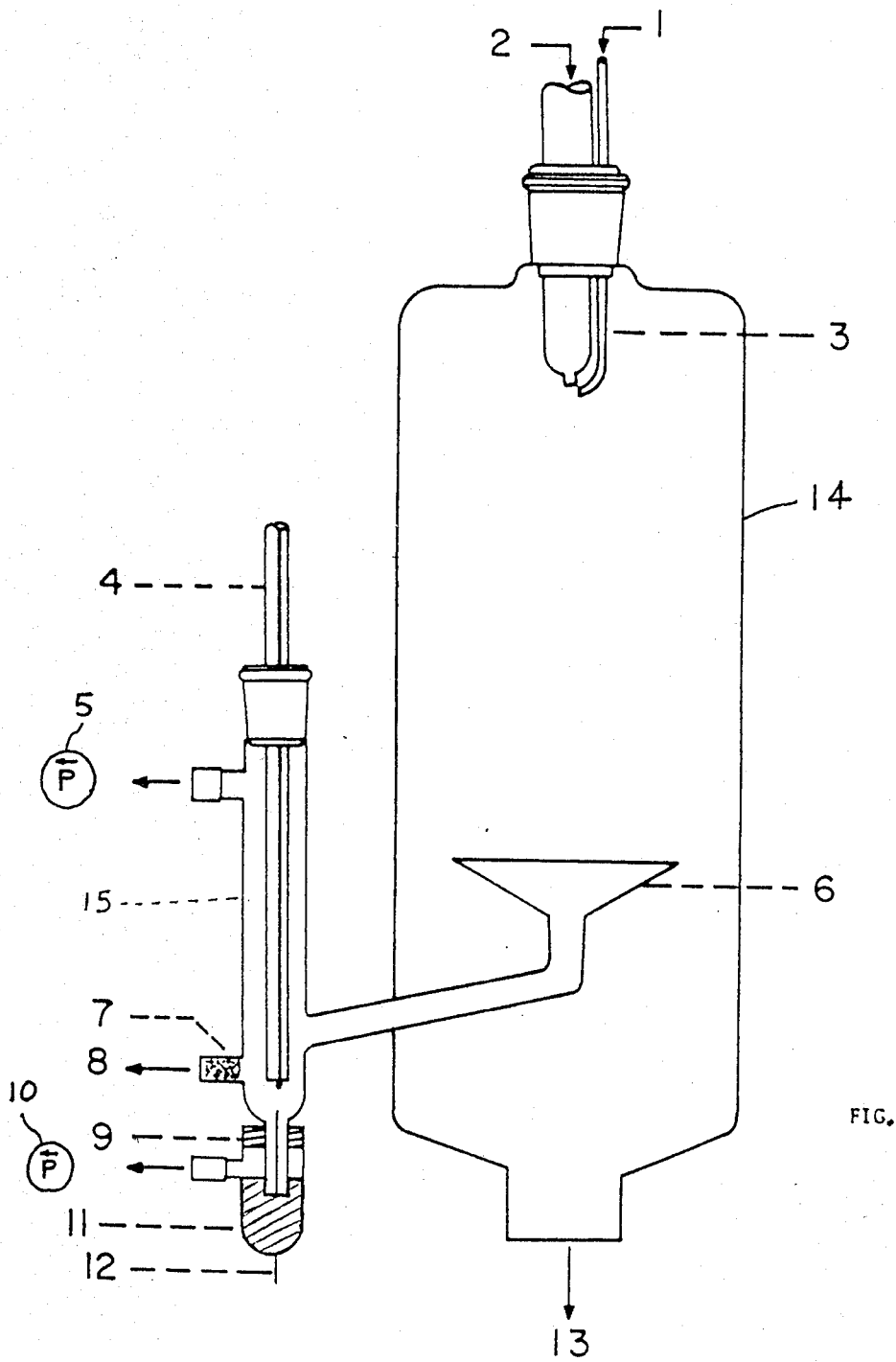
FIG. 1 is a general view of the system which illustrates the vessel and polarographic cell.

The automatic cell for polarographic analysis according to the present invention is very simple, as is evident from the attached FIG. 1. The sample to be analyzed is drawn through a tube (1) into a vessel (14) and deaerated in the nebulizer (3) by means of a stream of nitrogen introduced through a tube (2). It has been found that in this manner the deaeration of the sample is very rapid, being completed in less than twenty seconds for a sample of 10 mls volume. The deaerated sample is collected by a funnel-shaped collector (6) located inside said vessel (14). The location of the collector is critical for an accurate analysis. It should be located far enough from the nebulizer in order to effect the rapid and complete deaeration of the sample and close enough in order to ensure the collection of a major portion of the deaerated sample. The distance found to represent a good compromise is about 80 to 100 mm from the nebulizer nozzle. The shape of the collector is also determinant in the gathering of the maximum amount of the deaerated sample. It was found that the funnel shape is the most suitable, fulfilling the requirements enumerated above.

From the collector the deaerated sample is conveyed to the polarographic cell proper (15) by means of a feed pump (5). The said polarographic cell consists of a dropping mercury electrode (4) and a ceramic filter (7) connected to a reference electrode (8) and a platinum wire (12) which serves as a counter-electrode. A valve at the bottom of the polarographic cell serves for removal of the sample after analysis.

The preferred embodiment shown in FIG. 1 utilizes a mercury outlet valve because of its clear advantages, such as prolonged service life and complete removal of the sample. The mercury valve consists of a mercury pool (11) into which is immersed a thin tube connected to the polarographic cell proper, the tube both restraining any free flow of the sample and serving as a sleeve for shielding the platinum wire. Before new analysis is made, the solution is pumped out of the cell through the mercury valve by the scavenging pump (10). Although useful and practical, the valve, as such, is not essential to the gist of the present invention, and a person skilled in the art may select any other means or type of valve for the removal of the sample. At the bottom of the vessel (14) an outlet (13) serves for the withdrawal of remnants of the sample which have not been caught by the collector (6).

The polarographic analyzer which utilizes the automatic cell according to the present invention has been found to be most useful in the analysis of a broad range of cations ($Zn^{+2}$, $Cd^{+2}$, $Pb^{+2}$ etc.) and a number of organic compounds such as fumaric acid.

The results obtained with the automatic cell according to the present invention have shown to be very accurate, while the extremely short time required for the analyses distinguishes it favourably from prior art models.

The automatic polarographic cell has yielded results in which the reproducibility of the measurements of peak height was found to be even less than 1%. The cell can be used in conjunction with all the conventional modern accessories utilized with the known polarographic analyzers, such as microprocessor control, automatic scale expansion, and an autoranging capability.

An analysis of substances in solution by means of the cell of the present invention will proceed as follows (see FIG. 1). The solution to be analyzed is introduced through a tube (1). Upon depressing the starter button of the apparatus containing the cell (not shown) the scavenging pump (10) is actuated and removes the previous sample. Following this the stream of nitrogen and the feed pump (5) are switched on automatically, whereby the new sample is drawn through said tube (1) into the vessel (14) via the nebulizer (3). The sample thus deaerated is collected by the collector (6) under the influence of the feed pump (5) and drawn into the polarographic cell proper (15). It has been found advisable to stop the action of the scavenging pump (10) a few seconds after starting up the feed pump (5), since this aids in the complete removal of traces of the previous sample. The feed pump (5) and the stream of nitrogen are stopped automatically when the solution in the cell (15) reaches the dropping mercury electrode. This is accomplished by electronic means known to the art. Ten seconds after the mercury drop has become detached from the capillary tube (4) scanning of the potential is activated automatically by electronic means known to the art and a complete polarogram is recorded within about ten seconds.

Figure 2:
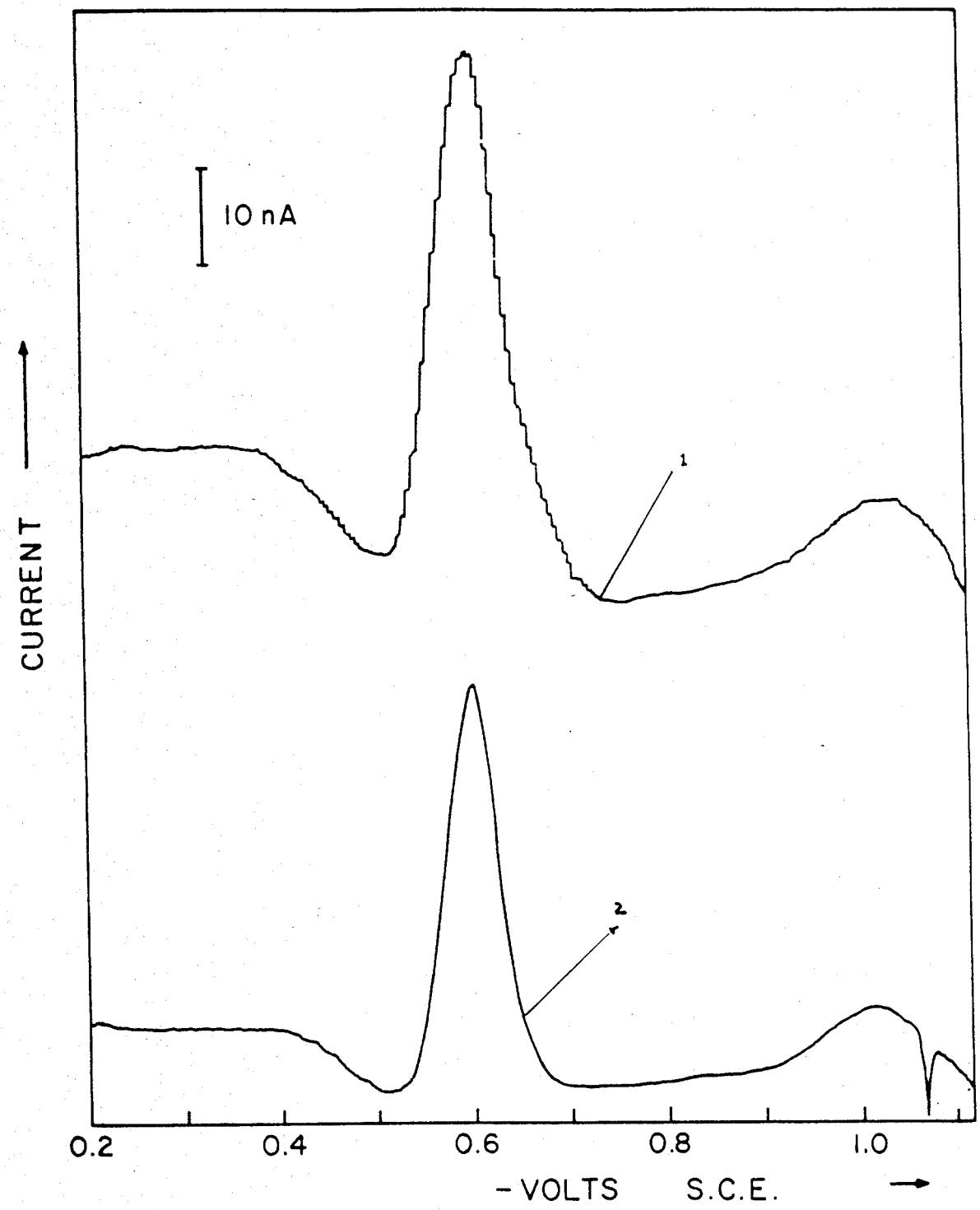
FIG. 2 illustrates in a graphic form the results of analysis.

The results of analysis with the automatic polarographic cell according to the present invention are very accurate, In FIG. 2 are presented two polarograms obtained in the determinations of a same aqueous solution containing $7 \times 10^{-7}M$ $Cd^{++}$. The graph (1) was obtained with Princeton Applied Research's Differential Pulse Polararograph and graph (2) was obtained with the automatic polarograph according to the present invention. It appears that the results are substantially the same.

Figure 3:
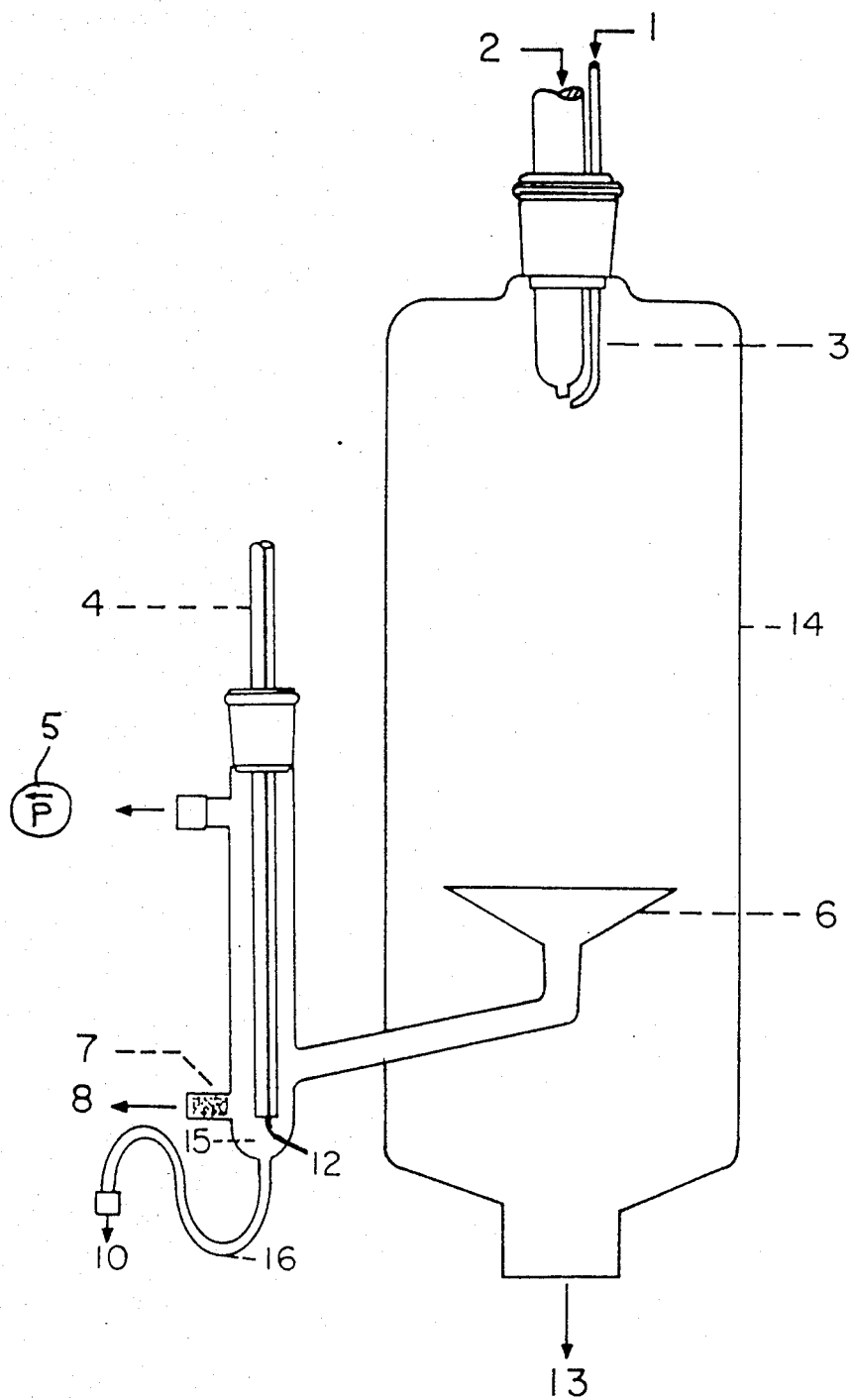
FIG. 3 represents a particular embodiment using a syphon-type valve.

According to another embodiment as illustrated in FIG. 3, no valve at all is present, the sample after analysis being removed from the polarographic cell (15) by a syphon-type device (16) located at the bottom of said cell (15). The description of the parts of the automatic cell illustrated in FIG. 3 are the same as these given for FIG. 1, except the omission of the mercury valve (11) mentioned therein, which is replaced by the syphon-type device (16). The advantage of the device according to this embodiment is its simplicity without any mechanical problems or troubles during operation such as clogging. Actually the device according to this embodiment might have an unlimited service life.

While the invention has been described by the above Example with the aid of certain preferred embodiments as described and illustrated referring to the attached FIGS. 1 and 3, it will be understood that it is not intended to limit the invention to these particular embodiments. It is on the contrary, intended to cover any alternatives, modifications, and equivalents, as may fall within the scope of the invention as defined by the appended claims.

I claim:

1. An automatically operated polarographic analyzing system for analyzing discrete samples comprising:
   a vessel including in an upper portion means for deaerating each one of said samples comprising a nebulizer and a stream of inert gas;
   collector means for collecting successive ones of said deaerated samples and an outlet for the exit of excess substances;
   a polarographic cell including a dropping mercury electrode, said cell being external to said vessel and connected to said collector means by means of tubing passing through a wall of said vessel;
   first pump means, coupled with said polarographic cell, defining means for moving a sample from said collector means to said polarographic cell for analysis, and second pump means, coupled with said polarographic cell, defining means for removing the sample after its analysis, said removing means being disposed below said dropping mercury electrode;
   a platinum wire extending below the dropping mercury electrode of said polarographic cell and passing out of said polarographic cell; and
   an outlet, close to the bottom end of the polarographic cell, connected to a reference electrode.

2. An automatically operated polarographic analyzer according to claim 1, wherein said removing means consists of a valve.

3. An automatically operated polarographic analyzer according to claim 2, wherein said valve is a mercury valve.

4. An automatically operated polarographic analyzer according to claim 1, wherein said removing means consists of a syphon-type device.

5. An automatically operated polarographic analyzer according to claim 1, wherein said nebulizer is activated by a stream of nitrogen gas.

6. An automatically operated polarographic analyzer according to claim 1, wherein said collector has a funnel-like shape.

7. An automatically operated polarographic analyzer according to claim 6, wherein said collector is located at a distance of between 80 and 100 mm from the nebulizer.

8. An automatically operated polarographic analyzer according to claim 1, used in conjunction with an automatic scale expansion and autoranging instrument.

9. An automatically operated polarographic analyzer according to claim 1, used in conjunction with a microprocessor control.

10. An automatically operated polarographic analyzing system for analyzing discrete samples comprising:
    a vessel including therein means for deaerating said samples comprising a nebulizer and a stream of inert gas; collector means for collecting the deaerated sample; and an outlet for the exit of excess substances;
    a polarographic cell including a dropping mercury electrode, said cell being external to said vessel and connected to said collector by means of tubing passing through the wall of said vessel;
    means in line with said polarographic cell, for removing the sample after analysis;
    a connecting member between said removing means and an external pump;
    a connecting member between said polarographic cell and another external pump;
    a platinum wire extending below the dropping mercury electrode of said polarographic cell and passing out of said polarographic cell; and
    an outlet, close to the bottom end of the polarographic cell, connected to a reference electrode.

* * * * *